(12) United States Patent
Nagashima et al.

(10) Patent No.: US 11,172,657 B2
(45) Date of Patent: Nov. 16, 2021

(54) METHOD FOR DEVELOPING ORGAN THAT LACKS SPECIFIC FUNCTIONAL CELL

(71) Applicant: PORMEDTEC CO., LTD., Kanagawa (JP)

(72) Inventors: Hiroshi Nagashima, Kawasaki (JP); Hitomi Matsunari, Kawasaki (JP); Kazuaki Nakano, Kawasaki (JP); Koki Hasegawa, Kawasaki (JP)

(73) Assignee: PORMEDTEC CO., LTD., Kanagawa (JP)

( * ) Notice: Subject to any disclaimer, the term of this patent is extended or adjusted under 35 U.S.C. 154(b) by 0 days.

(21) Appl. No.: 16/638,440

(22) PCT Filed: Sep. 18, 2018

(86) PCT No.: PCT/JP2018/034390
§ 371 (c)(1),
(2) Date: Feb. 11, 2020

(87) PCT Pub. No.: WO2019/059158
PCT Pub. Date: Mar. 28, 2019

(65) Prior Publication Data
US 2020/0165633 A1    May 28, 2020

(30) Foreign Application Priority Data
Sep. 19, 2017  (JP) .............................. JP2017-178552

(51) Int. Cl.
*A01K 67/027* (2006.01)
*C12N 15/877* (2010.01)

(52) U.S. Cl.
CPC ........ *A01K 67/0275* (2013.01); *A01K 67/027* (2013.01); *C12N 15/8778* (2013.01); *A01K 2227/108* (2013.01)

(58) Field of Classification Search
CPC .............. A01K 67/027; A01K 67/0275; A01K 2207/25; A01K 2217/05; A01K 2217/15; A01K 2217/206; A01K 2217/10; A01K 2217/108
See application file for complete search history.

(56) References Cited

U.S. PATENT DOCUMENTS

| | | | |
|---|---|---|---|
| 6,060,049 A | 5/2000 | Beschorner | |
| 6,071,697 A | 6/2000 | Sosa-Pineda et al. | |
| 6,147,275 A | 11/2000 | Vale et al. | |
| 6,525,242 B1 | 2/2003 | Wu et al. | |
| 7,122,357 B2 * | 10/2006 | Sander-Struckmeier | ................... A61K 38/465 435/183 |
| 2004/0028658 A1 | 2/2004 | Faustman | |
| 2011/0067125 A1 | 3/2011 | Nakauchi et al. | |
| 2011/0218191 A1 | 9/2011 | Johnston | |
| 2016/0278350 A1 | 9/2016 | Ayares | |

FOREIGN PATENT DOCUMENTS

| | | |
|---|---|---|
| JP | 7-509363 A | 10/1995 |
| JP | 9-500618 A | 1/1997 |
| JP | 2000-510000 A | 8/2000 |
| JP | 2002-509736 A | 4/2002 |
| JP | 2003-512846 A | 4/2003 |
| JP | 2005-535732 A | 11/2005 |
| JP | 2013-501528 A | 1/2013 |
| JP | 2013-521253 A | 6/2013 |
| WO | WO 94/02601 A1 | 2/1994 |
| WO | WO 2008/010100 A2 | 1/2008 |
| WO | WO 2010/021390 A1 | 2/2010 |
| WO | WO 2011/133284 A1 | 10/2011 |

OTHER PUBLICATIONS

Li et al J Vis Exp. Jan. 9, 2018(131):abstract only (Year: 2018).*
Naito et al. J Reprod Fert 113:137-143, 1998 (Year: 1998).*
Raina et al. Gene 96-100, 2015 (Year: 2015).*
Dolatshad et al. Mammalian Genome 26:598-608, 2015 (Year: 2015).*
Matsunari et al. PNAS 110(12):4557-4562, Mar. 19, 2013 (Year: 2013).*
Matsunari et al. Reproduction, Fertility and Development, (2014) vol. 26, No. 1, pp. 127-128. Abstract No. 26. Meeting Info: Annual Conference of the International Embryo Transfer Society, IETS 2014. Reno, NV, United States. Jan. 11, 2014-Jan. 14, 2014 ISSN: 1031-3613. (Year: 2014).*
Nasr Esfahani et al. International Journal of Fertility and Sterility, (Summer 2014) vol. 8, Supp. SUPPL. 1, p. 12. Abstract No. I-8. Meeting Info: 15th Congress on Reproductive Biomedicine and 9th Royan Nursing and Midwifery Seminar. Tehran, Iran, Islamic Republic of. Sep. 3, 2014-Sep. 5, 2014. (Year: 2014).*
Extended European Search Report dated Apr. 19, 2021, in European Patent Application No. 18858805.7.
Hale et al. "The homeodomain protein PDX1 is required at mid-pancreatic development for the formation of the exocrine pancreas," Developmental Biology (2005), vol. 286, pp. 225-237.
Stfrauss et al., "Use of Continuous Glucose Monitoring System in Goettingen Minipigs, with a Special Focus on the Evaluation of Insulin-Dependent Diabetes," Transplantation Proceedings (2008), vol. 40, pp. 536-539.
Extended European Search Report dated Apr. 19, 2021, in European Patent Application No. 18858805.7.
Hale et al. "The homeodomain protein PDX1 is required at mid-pancreatic development for the formation of the exocrine pancreas," Developmental Biology (2005), vol. 286, pp. 225-237.
Stfrauss et al., "Use of Continuous Glucose Monitoring System in Goettingen Minipigs, with a Special Focus on the Evaluation of Insulin-Dependent Diabetes," Transplantation Proceedings (2008), vol. 40, pp. 536-539.

(Continued)

*Primary Examiner* — Marcia S Noble
(74) *Attorney, Agent, or Firm* — Birch, Stewart, Kolasch & Birch, LLP

(57) ABSTRACT

Provided is a method for developing a secondary organ by using a non-human animal in which organ formation is inhibited, for the purpose of establishing a process for producing a functional cell such as a β cell within the body of an animal such as a pig, the method including the step of raising a newborn or a fetus of the non-human animal in which organ formation is inhibited by complementing at least a part of the function of the organ whose formation is inhibited.

8 Claims, 9 Drawing Sheets
(2 of 9 Drawing Sheet(s) Filed in Color)

(56) References Cited

OTHER PUBLICATIONS

Takebe et al., "Vascularized and Complex Organ Buds from Diverse Tissues via Mesenchymal Cell-Driven Condensation," Cell Stem Cell (2015), vol. 16, pp. 556-565.
International Search Report for PCT/JP2018/034390 (PCT/ISA/210) dated Dec. 25, 2018.

* cited by examiner

|  | Day23 | | | Day60 | | |
|---|---|---|---|---|---|---|
| Parameters | WT(n-4) | Pdx1-Hes1 | TREATED GROUP (n-4) | WT(n-4) | Pdx1-Hes1 | TREATED GROUP (n-3) |
| TP (g/dl) | 4.725±0.13 | 4.75±0.29 | | 5.5525±0.02 | 5.5±0.1 | |
| ALB (g/dl) | 2.925±0.16 | 3.075±0.44 | | 4.75±0.06 | 4.7±0.09 | |
| UA (mg/dl) | 0.35±0.03 | 0.425±0.02 | | 0.275±0.08 | 0.4±0.03 | |
| BUN (mg/dl) | 15.375±1.43 | 24.825±2.94 | | 10.55±0.68 | 18.1±1.1 | |
| CRE (mg/dl) | 0.55±0.03 | 0.45±0.09 | | 0.675±0.03 | 1.1±0.22 | |
| Na (mEq/l) | 139.5±0.5 | 128±3.03 | | 143.75±0.63 | 132.3±0.33 | |
| K (mEq/l) | 3.975±0.11 | 4.225±0.08 | | 3.475±0.08 | 4.9±0.42 | |
| Cl (mEq/l) | 98±0.71 | 94.5±2.5 | | 105.5±0.87 | 96.3±0.33 | |
| Ca (mg/dl) | 10.1±0.27 | 9.6±0.24 | | 10.275±0.09 | 10.3±0.21 | |
| IP (mg/dl) | 10.475±0.18 | 9.075±0.33 | | 10.055±0.76 | 9.6±0.17 | |
| GOT (IU/l) | 44±4.6 | 28.25±3.42 | | 32±4.18 | 27.7±12.25 | |
| GPT (IU/l) | 59.25±3.75 | 55.75±3.17 | | 35±2.71 | 38.7±0.88 | |
| ALP (IU/l) | 1345±42.1 | 2078.75±166.8 | | 1118±66.04 | 14867±183.24 | |
| γ-GT (IU/l) | 27.5±0.65 | 46.5±6.6 | | 27.25±2.75 | 45±3.61 | |
| LIP (IU/l) | 45.25±8.78 | 41.25±2.69 | | 35.5±9.54 | 33.7±2.03 | |
| TCHO (mg/dl) | 87±12.52 | 84.5±5.52 | | 88±8.42 | 85.3±6.89 | |
| TG (mg/dl) | 69±5.64 | 350.25±67.91 | | 39.75±4.21 | 261.25±107.72 | |
| HDL-C (mg/dl) | 44.5±8.74 | 55.5±5.24 | | 40±5.99 | 45±3.06 | |
| TBIL (mg/dl) | 0.35±0.03 | 1.15±0.14 | | 0.25±0.06 | 0.3±0.09 | |
| Mg (mg/dl) | 2.375±0.08 | 2.1±0.07 | | 2.4±0.09 | 2.6±0.03 | |
| Insulin (ng/mg) | 0.9475±0.13 | N.D | | 5.7625±0.76 | N.D | |
| 1.5-AG (pg/ml) | 2.425±0.19 | N.D | | 6.25±0.95 | N.D | |
| Glucagon (pg/ml) | 150±6.75 | 287.5±58.21 | | 178.75±5.27 | 262±22.81 | |
| GLU (mg/dl) | 102.5±3.71 | 406.5±16.03 | | 111.25±2.87 | 636.7±78.45 | |
| AMYL (IU/l) | 1302.25±170.04 | 924.75±175.38 | | 1659.5±209.17 | 1061±258.79 | |
| LDH (IU/l) | 900±0 | 659.25±40.98 | | 780.25±61.96 | 543.7±21.06 | |
| NH3 (μg/dl) | 125.75±22.37 | 123.25±12.85 | | 115±17.38 | 174±2.65 | |

FIG.3

| | AGE IN DAYS | No | BODY WEIGHT (kg) | PANCREAS WEIGHT (g) | PANCREAS WEIGHT / BODY WEIGHT |
|---|---|---|---|---|---|
| *Pdx1-Hes1* | 38 | #M148-5 | 2.03 | 0.72 | 0.03% |
| | 80 | #M220-4 | 19.04 | 5.11 | 0.03% |
| | | #M220-6 | 17.45 | 4.12 | 0.02% |
| | | #M148-3 | 23.51 | 5.45 | 0.02% |
| | | Ave | 20[a] | 4.89[a] | 0.02%[a] |
| WT | 80 | #M220-5 | 29.50 | 42.34 | 0.14% |
| | | #M220-7 | 40.00 | 63.27 | 0.16% |
| | | #M148-9 | 29.00 | 45.02 | 0.16% |
| | | #M148-10 | 36.00 | 64.96 | 0.18% |
| | | Ave | 33.62[b] | 53.89[b] | 0.16%[b] |

FIG.7

Figure 8
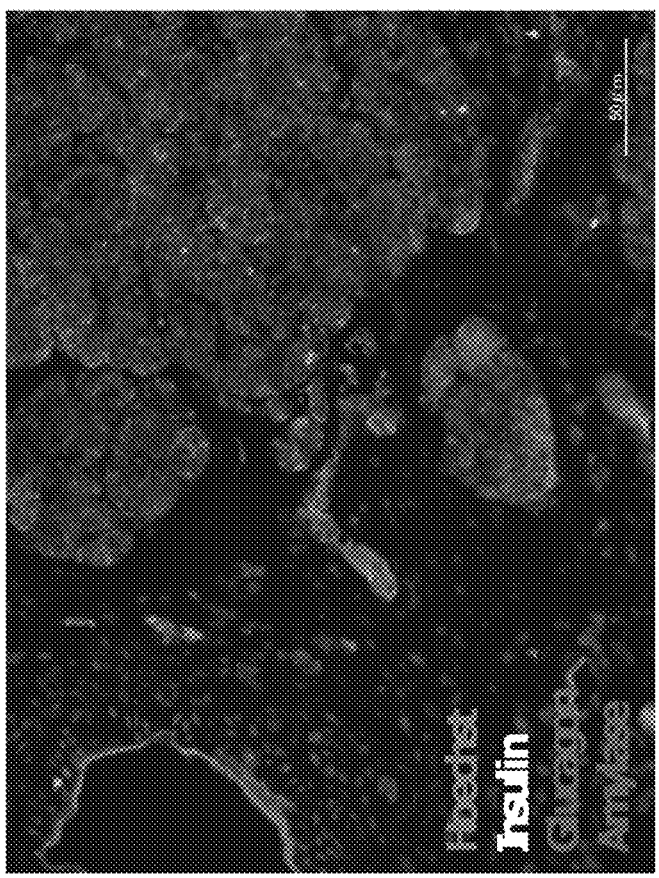
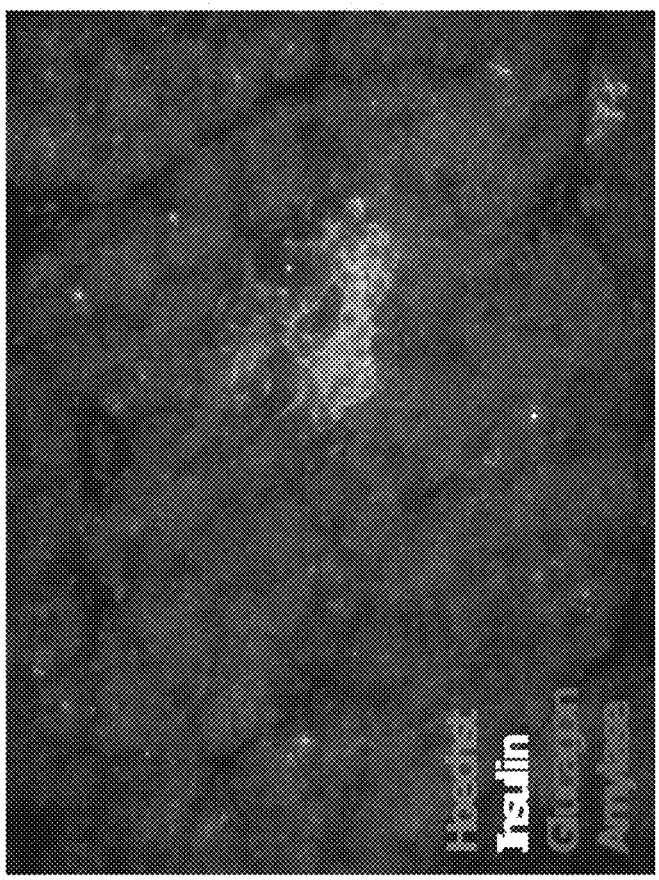

METHOD FOR DEVELOPING ORGAN THAT LACKS SPECIFIC FUNCTIONAL CELL

TECHNICAL FIELD

The present invention relates to a method for developing a secondary organ by using a non-human animal in which organ formation is inhibited. The present invention also relates to a non-human animal that has a secondary organ lacking a specific functional cell. Furthermore, the present invention relates to a method for producing a cell. Furthermore, the present invention relates to a secondary organ lacking a specific functional cell.

BACKGROUND ART

Blastocyst complementation method is a method for forming an organ derived from cells of a normal animal by injecting the cells of the normal animal into a blastocyst of an animal lacking an organ. Utilizing this blastocyst complementation method, the present inventors have successfully generated a chimeric pig that had a pancreas derived from a donor by injecting an embryo from a normal pig (donor embryo) into an embryo from a pig lacking a pancreas (host embryo) and allowing the host embryo to develop in the body of a surrogate parental pig (Non Patent Literature 1). Although the chimera was generated between pigs in Non Patent Literature 1, a pig that has a human pancreas is expected to be generated by using a human pluripotent stem cell as a donor and such a human pancreas may be used for islet transplantation.

CITATION LIST

Non Patent Literature

Non Patent Literature 1: Matsunari et al., PNAS 110: 4557-4562 (2013)

SUMMARY OF INVENTION

Technical Problem

If a human organ (for example, a pancreas) or a functional cell (for example, a β cell) can be successfully produced within the body of an animal such as a pig, the problem of donor shortage in transplantation therapy can be solved.

On the other hand, under the existing circumstances, there are many ethical problems to be solved in transplantation in which a chimeric state between a human and an animal is induced at an early stage of development and an organ or functional cell thus produced is transplanted into a human. In comparison with this, it is believed that there is a lower ethical barrier to performing cell transplantation in which a chimeric state between a human and an animal is not induced at an early stage of development, a specific functional cell (for example, a β cell) that can establish itself in a human is grown in an organ of an animal such as a pig, and the functional cell is transplanted into a human.

However, until now, there has been no known organ or tissue suitable for cell growth to perform such cell transplantation, wherein the organ or the tissue lacks only the specific functional cell (for example, a β cell) and serves as an environment for producing and growing the above described specific functional cell.

Under such circumstances, it is an object of the present invention to provide means for producing a functional cell within an animal body.

Solution to Problem

A newborn piglet in which pancreas formation is inhibited dies about three days after birth due to hyperglycemia and dyspepsia. The present inventors raised such a newborn by administering insulin and a digestive enzyme combination thereto so that the newborn survived, and have found that as the newborn grew, pancreas-like tissue formed in a space where a pancreas would have formed under normal circumstances. The present inventors also have found that this pancreas-like tissue came to produce a digestive enzyme and glucagon but did not come to produce insulin (in other words, no β cell formed). It was totally unexpected that this pancreas-like tissue that had not been found during the fetal stage started to develop by the above described raising and further formed into an incomplete pancreas in which no insulin-producing β cell formed while other endocrine cells and/or an exocrine cell existed. It was also totally unexpected that only insulin was not produced although the digestive enzyme and glucagon were produced.

The β cell-lacking pancreas-like tissue formed by the above described raising has an environment (such as a tissue structure and function) other than the β cell and is believed to be an excellent "vacant niche" for growing a progenitor cell of the β cell and a pluripotent stem cell. Therefore, it is believed that a human β cell can be produced efficiently by transplanting, for example, a progenitor cell of a β cell derived from a human into the β cell-lacking pancreas-like tissue.

The present invention has been accomplished on the basis of the above described findings.

Specifically, the present invention provides the following [1] to [18].

[1] A method for developing a secondary organ by using a non-human animal in which organ formation is inhibited, including the step of:
(1) raising a newborn or a fetus of the non-human animal in which organ formation is inhibited by complementing at least a part of the function of the organ whose formation is inhibited.
[2] The method according to [1], wherein the secondary organ develops in such a manner that at least a part of the function complemented by the raising is impaired.
[3] The method according to [1] or [2], wherein the secondary organ is an organ lacking a specific functional cell.
[4] The method according to [3], wherein the functional cell is a β cell.
[5] The method according to any of [1] to [4], wherein organ formation is inhibited by genetic modification of the non-human animal in step (1).
[6] The method according to any of [1] to [5], wherein the organ whose formation is inhibited is a pancreas and complementation of the function of the pancreas whose formation is inhibited is performed by administering at least insulin and a digestive enzyme.
[7] The method according to [5], wherein the genetic modification is overexpressing a Hes1 gene under the control of a Pdx1 promoter in the non-human animal.
[8] The method according to any of [1] to [7], wherein the non-human animal is a pig.
[9] A non-human animal obtained by raising a newborn or a fetus of a non-human animal in which organ formation is inhibited, wherein the non-human animal has a secondary organ lacking a specific functional cell.

[10] The non-human animal according to [9], wherein the organ is a pancreas and the functional cell is a β cell.

[11] The non-human animal according to [10], wherein the newborn or the fetus of the non-human animal is that in which organ formation is inhibited by overexpressing a Hes1 gene under the control of a Pdx1 promoter.

[12] The non-human animal according to any of [9] to [11], wherein the non-human animal is a pig.

[13] A secondary organ developed by raising a newborn or a fetus of a non-human animal in which organ formation is inhibited, wherein the secondary organ lacks a specific functional cell.

[14] The secondary organ according to [13], wherein the organ is a pancreas and the functional cell is a β cell.

[15] The secondary organ according to [14], wherein the newborn or the fetus of the non-human animal is that in which organ formation is inhibited by overexpressing a Hes1 gene under the control of a Pdx1 promoter.

[16] The secondary organ according to any of [13] to [15], wherein the non-human animal is a pig.

[17] The secondary organ according to any of [13] to [16], wherein a transplanted cell established itself in the secondary organ.

[18] A method for producing a cell within the body of a non-human animal, including the step of raising the non-human animal according to [1] or [2].

This specification encompasses the content described in the specification and/or drawing of Japanese Patent Application No. 2017-178552, which forms the basis of priority of this application.

Advantageous Effects of Invention

The present invention provides the method for developing a secondary organ by using a non-human animal in which organ formation is inhibited, the non-human animal that has a secondary organ lacking a specific functional cell, the method for producing a cell, and the secondary organ lacking a specific functional cell.

BRIEF DESCRIPTION OF DRAWINGS

This patent or application file contains at least one drawing executed in color. Copies of this patent or patent application publication with color drawing(s) will be provided by the Office upon request and payment of the necessary fee.

FIG. 3 shows a table showing blood biochemical parameters of the pig in which pancreas formation is inhibited and the wild type pig (23 days old and 60 days old).

FIG. 7 shows a table showing the body weight, the pancreas weight, and the ratio of pancreas weight to body weight of the pig in which pancreas formation is inhibited (upper row) and the wild type pig (lower row).

FIG. 8 shows a photograph showing the result of immunostaining for amylase of the pancreatic tissue of the pig in which pancreas formation is inhibited (right) and the wild type pig (left). An amylase-positive cell was observed in the pancreatic tissue of the pig in which pancreas formation is inhibited.

DESCRIPTION OF EMBODIMENTS

Figure 1:
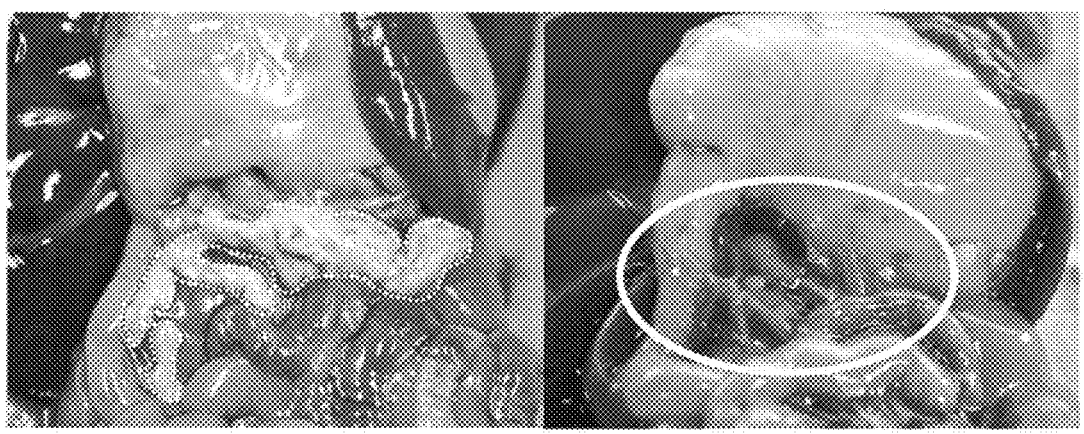
FIG. 1 shows a photograph of internal organs of a pig in which pancreas formation is inhibited (right) and a wild type pig (left).

Hereinafter, the present invention is described in detail.
(A) Method for Developing Secondary Organ by Using Non-Human Animal in which Organ Formation is Inhibited The method of the present invention for developing a secondary organ by using a non-human animal in which organ formation is inhibited includes the step of (1) raising a newborn or a fetus of the non-human animal in which organ formation is inhibited by complementing at least a part of the function of the organ whose formation is inhibited.

Examples of the organ whose formation is to be inhibited may include a pancreas, and the organ may be any organ other than the pancreas as long as the newborn or the fetus can survive even if formation of the organ is inhibited. Examples of the organ other than the pancreas may include a kidney.

Inhibition of organ formation can be performed by genetic modification that modifies a gene of the non-human animal having the organ. For example, inhibition of pancreas formation can be performed by using a Pdx1-Hes1 gene composed of a Hes1 gene linked to a Pdx1 gene promoter, specifically by overexpressing the Hes1 gene under the control of the Pdx1 promoter (Matsunari et al., PNAS 110: 4557-4562 (2013)). Organ formation may also be inhibited by administration of an agent. On the other hand, the effect of the present invention cannot be achieved when organ formation is disabled by destroying the Pdx1 gene. Inhibition of kidney formation can be performed, for example, by overexpressing a Six2-Notch2 gene (Fujimura et al., J Am Soc Nephrol, 21:803-810, 2010) and by inhibiting or suppressing expression of a gene that controls kidney development, such as Sall1 and Pax2.

The animal to be subjected to inhibition of organ formation may be any animal as long as the animal is not a human, but is preferably a mammal. Specific examples of the animal may include a mouse, a rat, a hamster, a guinea pig, a rabbit, a dog, a cat, a horse, a cow, a sheep, a pig, a goat, and a monkey. Among these, a pig can be a preferable animal.

In the present invention, a "secondary organ" means an organ-like tissue that was formed in a site within the body of a non-human animal by raising and growing the animal, wherein the site is a site where a formation-inhibited organ (for example, a pancreas) would have formed under normal circumstances. The secondary organ may have 100% or a part of the function of the normal organ. Examples of a preferable secondary organ may include a secondary organ lacking a specific functional cell. In this context, a "functional cell" means a cell that is included in an organ and has some function, such as an α cell, a β cell, and a γ cell in the pancreas. Examples of a preferable functional cell may include a β cell. Examples of a preferable organ lacking a specific functional cell may include a pancreas lacking a β cell.

A newborn or a fetus of the non-human animal in which organ formation is inhibited can be obtained by a known method. For example, a newborn or a fetus of a pig whose pancreas formation is inhibited by using the Pdx1-Hes1 gene can be obtained by the following methods (a) to (d).

(a) Artificial insemination is performed on a wild type female by using a sperm into which the Pdx1-Hes1 gene has been integrated.
(b) In vitro fertilization is performed on an egg derived from a wild type female by using a sperm into which the Pdx1-Hes1 gene has been integrated.
(c) A male that produces a sperm into which the Pdx1-Hes1 gene has been integrated is mated with a wild type female.
(d) A cloned pig is generated by nuclear transplantation using a somatic cell into which the Pdx1-Hes1 gene has been integrated.

"Complementing at least a part of the function of the organ whose formation is inhibited" means administering an enzyme or a hormone that the organ would produce under normal circumstances or an agent having a function equivalent thereto; transplanting, for example, a cell that substitutes for the function of the organ; using a device that substitutes for the function of the organ; or the like. The function of the organ does not need to be fully complemented and may be partially complemented as long as the newborn or the fetus of the non-human animal can survive. A specific complementation method can be decided as appropriate depending on the organ type. For example, for complementing the function of the pancreas, all or some of the hormones and digestive enzymes produced by the pancreas may be administered. Specifically, the pancreas produces hormones such as glucagon, insulin, and somatostatin, all or some of which can be administered. The pancreas also produces digestive enzymes such as a proteolytic enzyme (chymotrypsin and trypsin), a polysaccharide-degrading enzyme (amylase), and a lipolytic enzyme (lipase), all or some of which can be administered. Furthermore, instead of administering the actual hormones and/or digestive enzymes produced by the pancreas, an agent having a function equivalent thereto may be administered. Examples of a preferable raising method for complementing the function of the pancreas may include a raising method that includes administering insulin and the digestive enzyme. Examples of the digestive enzyme to be administered in this context may include a proteolytic enzyme, a polysaccharide-degrading enzyme, and a lipolytic enzyme.

Raising the newborn or the fetus can be performed in accordance with an ordinary method except that at least a part of the function of the formation-inhibited organ is complemented.

As described below, in some cases, human-derived cells are transplanted into the secondary organ formed by the above described method, and such heterotransplantation causes rejection. To avoid this rejection, it is preferable to modify a gene of the non-human animal where the secondary organ is developed, thereby inducing immunodeficiency (SCID). Methods for inducing such immunodeficiency are reported in many publications, and the present inventors have generated an immunodeficient pig by knocking out an IL2RG gene (Watanabe et al., PLoS One 8(10): e76478 (2013)). Thus, induction of immunodeficiency can be performed according to description of such publications. It is also possible to induce immunological tolerance to a human-derived cell by transplanting a large quantity of human-derived cells into a fetus before immune system is established. Therefore, such a method may be used to avoid rejection caused by heterotransplantation.

The length of the raising period for developing the secondary organ is not particularly limited. When the developed secondary organ is intended to be used for a method described below for producing a functional cell, raising is continued until the functional cell is ready to be collected.

(B) Non-Human Animal

The non-human animal of the present invention is a non-human animal obtained by raising a newborn or a fetus of a non-human animal in which organ formation is inhibited, wherein the non-human animal has a secondary organ lacking a specific functional cell.

The non-human animal of the present invention can be used for the method described below for producing a functional cell, and furthermore can also be used as a model animal for a disease or a malformation. For example, when the specific functional cell that the non-human animal lacks is a β cell, which contributes to insulin production, the non-human animal can be used as a model animal for a complication caused by diabetes, such as retinopathy, nephropathy, neuropathy, angiopathy, and cataract.

The type of the functional cell, the type of the secondary organ lacking a specific functional cell, and the type of the animal to be subjected to inhibition of organ formation may be similar to those described in the above "Method for Developing Secondary Organ by Using Non-human Animal in which Organ Formation is Inhibited." The method for inhibiting organ formation and the method for raising a newborn or a fetus can also be performed in a similar manner to the above "Method for Developing Secondary Organ by Using Non-human Animal in which Organ Formation is Inhibited."

As described above, in this specification, a "non-human animal," which is a "product," is specified not by the structure or characteristic thereof but by a method for producing the same. The reason for this is that the "non-human animal" is an organism and thus has an extremely complicated structure and characteristic, and therefore carrying out work for specifying the structure and characteristic thereof requires remarkably excessive economic expense and time.

(C) Method for Producing Functional Cell

The inventive method for producing a functional cell includes the steps of (1) transplanting at least a progenitor cell of the functional cell or a pluripotent stem cell into the secondary organ of the non-human animal; and (2) inducing the progenitor cell or the pluripotent stem cell to the functional cell.

A "progenitor cell of a functional cell" means a cell that originates from a stem cell and can differentiate into a functional cell, and examples thereof include a progenitor cell of an α cell, a progenitor cell of a β cell, and a progenitor cell of a γ cell in the pancreas. Examples of a preferable progenitor cell of a functional cell may include the progenitor cell of a β cell. Instead of the progenitor cell of a functional cell, a pluripotent stem cell whose differentiation was appropriately induced may be transplanted. An embryonic stem cell (ES cell), an induced pluripotent stem cell (iPS cell), or the like can be used as the pluripotent stem cell. Other cells may also be transplanted in addition to the progenitor cell of a functional cell and the pluripotent stem cell. For example, in the case of the pancreas, a cell associated with pancreatic islet formation is preferably transplanted. Examples of the cell associated with pancreatic islet formation may include an interstitial cell, a cell involved in induction of a blood vessel, and an endocrine cell.

The main purpose of the inventive method for producing a functional cell is producing a functional cell for transplantation into a human, and therefore, the progenitor cell or pluripotent stem cell to be transplanted is preferably derived from a human.

The number of cells to be transplanted into the secondary organ can be decided as appropriate depending on the type of the animal, the cell type, the type of the secondary organ, and the like. For example, when the cells are transplanted into the pancreas of a pig, the number of cells is usually, without particular limitations, $1 \times 10^6$ to $5 \times 10^8$.

The timing for performing transplantation can be decided as appropriate depending on the cell type, the type of the secondary organ, the type of the animal, and the like. When the cells are transplanted into the pancreas of a pig, transplantation is usually performed, without particular limitations, at the timing when the pig is 10 to 90 days old.

When the cells to be transplanted are human-derived cells, heterotransplantation causes rejection. When the non-human animal into which cells are transplanted is the immunodeficient animal or the animal with induced immunological tolerance to human-derived cells as described above, rejection can be avoided. Otherwise, it is preferable to avoid rejection by administering an immunosuppressive agent (for example, ciclosporin) to the non-human animal.

Although the secondary organ lacking a specific functional cell lacks the specific functional cell, the secondary organ has other functional cells and tissues, and thus, the secondary organ is presumed to have an environment favorable for differentiation into the specific functional cell. Therefore, when progenitor cells or pluripotent stem cells are transplanted into this organ, the cells are expected to differentiate into the specific functional cells without requiring a particular treatment. However, a substance such as an agent and a growth factor may be injected into the secondary organ to promote differentiation into the specific functional cell.

The functional cells are collected from the secondary organ at an appropriate time after transplantation. The timing for collection can be decided as appropriate depending on the cell type, the type of the secondary organ, the type of the animal, and the like. When β cells are collected from the pancreas of a pig, the β cells are usually collected, without particular limitations, 1 to 12 months after transplantation.

Although a method other than the method of the present invention, for example, a blastocyst complementation method can be used to produce a human-derived functional cell in a non-human animal, the inventive method is superior to a conventional method in the following respects.

(a) In the blastocyst complementation method, human-derived cells are transplanted at an early stage of development such as a blastocyst stage. Such transplantation at an early stage of development leads to dilution of the human-derived cells. Specifically, some of the transplanted human-derived cells differentiate into functional cells but the majorities thereof differentiate into different cells other than the functional cells or disappear, which leads to a lower quantity of resulting human-derived functional cells. In contrast to this method, in the method of the present invention, human-derived cells are transplanted into an already differentiated organ. Therefore, it is expected that the majority of the transplanted cells differentiate into functional cells and abundant human-derived functional cells are obtained.

(b) In the blastocyst complementation method, human-derived cells are transplanted into the blastocyst. The cells included in the blastocyst are undifferentiated cells and these cells differentiate into adult cells over time. The transplanted human-derived cells cannot become functional cells in the end unless the transplanted cells themselves differentiate at the same pace as the differentiation progress of such host cells. Therefore, it is presumed that there are many human-derived cells that cannot become functional cells because of relation to the differentiation progress of the host cells. In the method of the present invention, human-derived cells are transplanted into an already differentiated organ, and therefore, the above described problem associated with the differentiation progress of the host cells is presumed not to occur.

(D) Secondary Organ

The secondary organ of the present invention is a secondary organ developed by raising a newborn or a fetus of a non-human animal in which organ formation is inhibited, wherein the secondary organ lacks a specific functional cell.

The type of the functional cell, the type of the secondary organ lacking a specific functional cell, and the type of the animal to be subjected to inhibition of organ formation may be similar to those described in the above "Method for Developing Secondary Organ by Using Non-human Animal in which Organ Formation is Inhibited." The method for inhibiting organ formation and the method for raising a newborn or a fetus can also be performed in a similar manner to the above "Method for Developing Secondary Organ by Using Non-human Animal in which Organ Formation is Inhibited."

EXAMPLES

Hereinbelow, the present invention will be described in more detail with reference to Examples, but the present invention is not limited to these Examples.

Example 1

Obtaining Newborn Piglet in which Pancreas Formation is Inhibited

The present inventors previously generated a chimeric pig that had a pancreas derived from a donor by injecting an embryo from a normal pig (donor embryo) into an embryo from a Pdx1-Hes1 gene-carrying and pig in which pancreas formation is inhibited (host embryo) and then allowing this to develop in the body of a surrogate parental pig (Matsunari et al., PNAS 110: 4557-4562 (2013)). A male of this chimeric pig can be naturally mated with a female wild type pig, thereby obtaining pancreas formation-inhibited newborns always at a certain ratio.

The newborn piglet in which pancreas formation is inhibited to be used in this Example was obtained by natural mating with such a chimeric pig.

Example 2

Raising Newborn Piglet in which Pancreas Formation is Inhibited

A newborn piglet in which pancreas formation is inhibited (precisely, that has only rudimentary pancreatic tissue) by carrying a Pdx1-Hes1 gene lacks an endocrine cell (for example, a β cell producing insulin) and an exocrine cell. Consequently, the piglet dies about three days after birth due to extreme hyperglycemia and dyspepsia.

Insulin and a digestive enzyme combination were administered as appropriate to such a newborn piglet in which pancreas formation is inhibited to bring the blood glucose level close to a normal level and induce individual growth and development of the pancreas.

1) Insulin Preparation:

Levemir (Novo Nordisk) was administered at a dose of 0.2 to 0.3 IU/kg twice a day, or Tresiba (Novo Nordisk) was administered once a day.

2) Insulin Administration Method:

Insulin was administered by subcutaneous injection or continuously administered with an insulin pump.

3) Digestive Enzyme Combination Agent:

A daily dose of 150 mg to 750 mg of Berizym (SHIONOGI & CO., LTD.) was mixed with a milk substitute or solid (powdered) laboratory chow and given to the piglet. Berizym contains lipase, cellulase, biodiastase, and pancreatin.

4) Laboratory Chow and Feeding Method:

From 0 to 7 days after birth, the piglet was fed with the milk substitute by a human or fed with milk by the mother pig. From 8 days after birth onward, the piglet was subjected to restricted feeding (the piglet is not allowed to eat ad libitum and is fed with a fixed daily amount of food) using a powdered milk substitute or powdered laboratory chow.

Example 3

Figure 2:
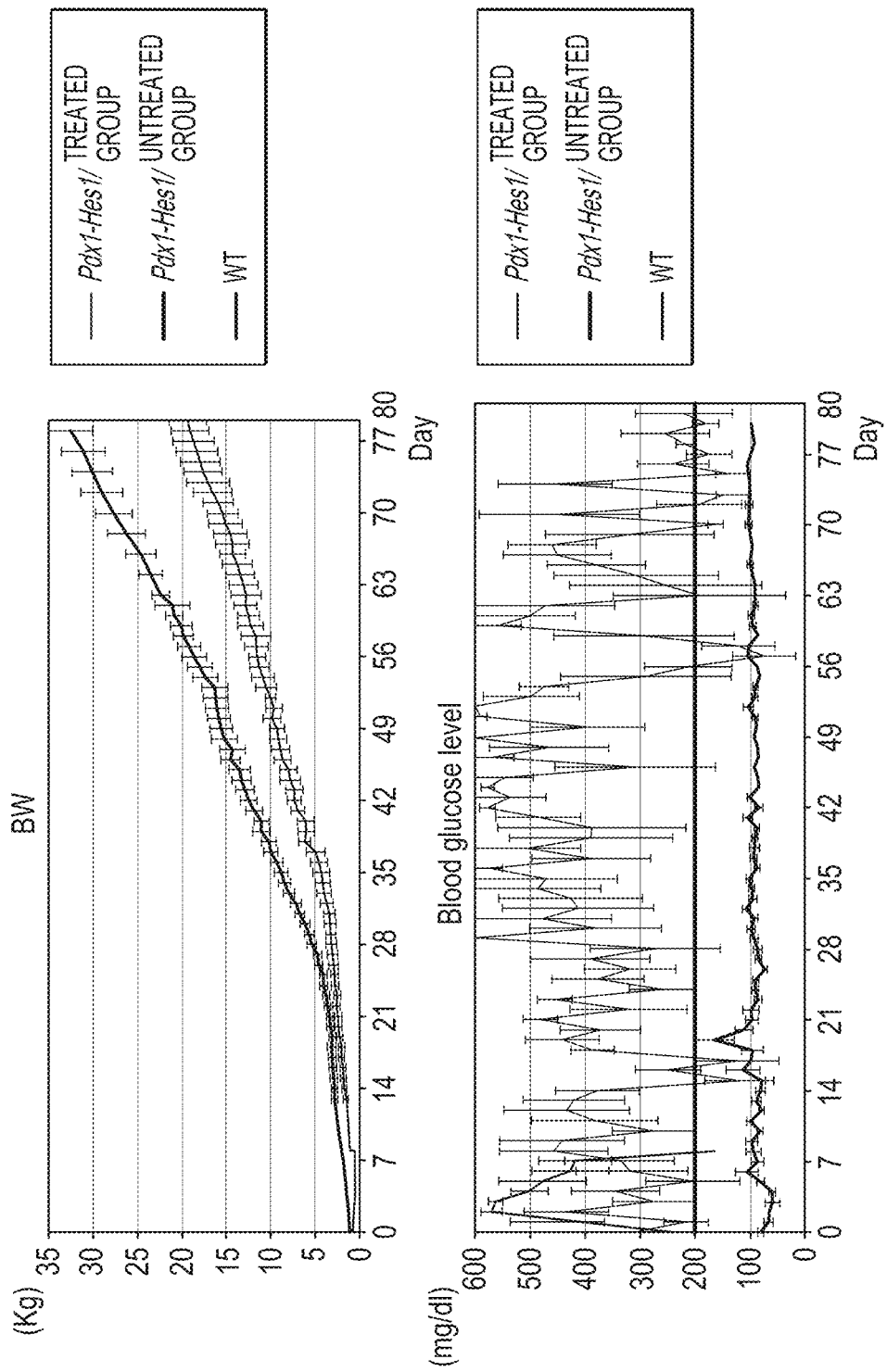
FIG. 2 shows a graph showing change over time in the weight (top) and the blood glucose level (bottom) of the pig in which pancreas formation is inhibited and the wild type pig.

Development of Pancreas by Supported Raising of Newborn Piglet in which Pancreas Formation is Inhibited 1) Controlled Blood Glucose Level and Growth:

When a newborn piglet in which pancreas formation is inhibited was raised according to the method described in Example 2, the blood glucose level thereof was controlled to some extent and the individual grew as shown in FIG. 2.

Figure 4:
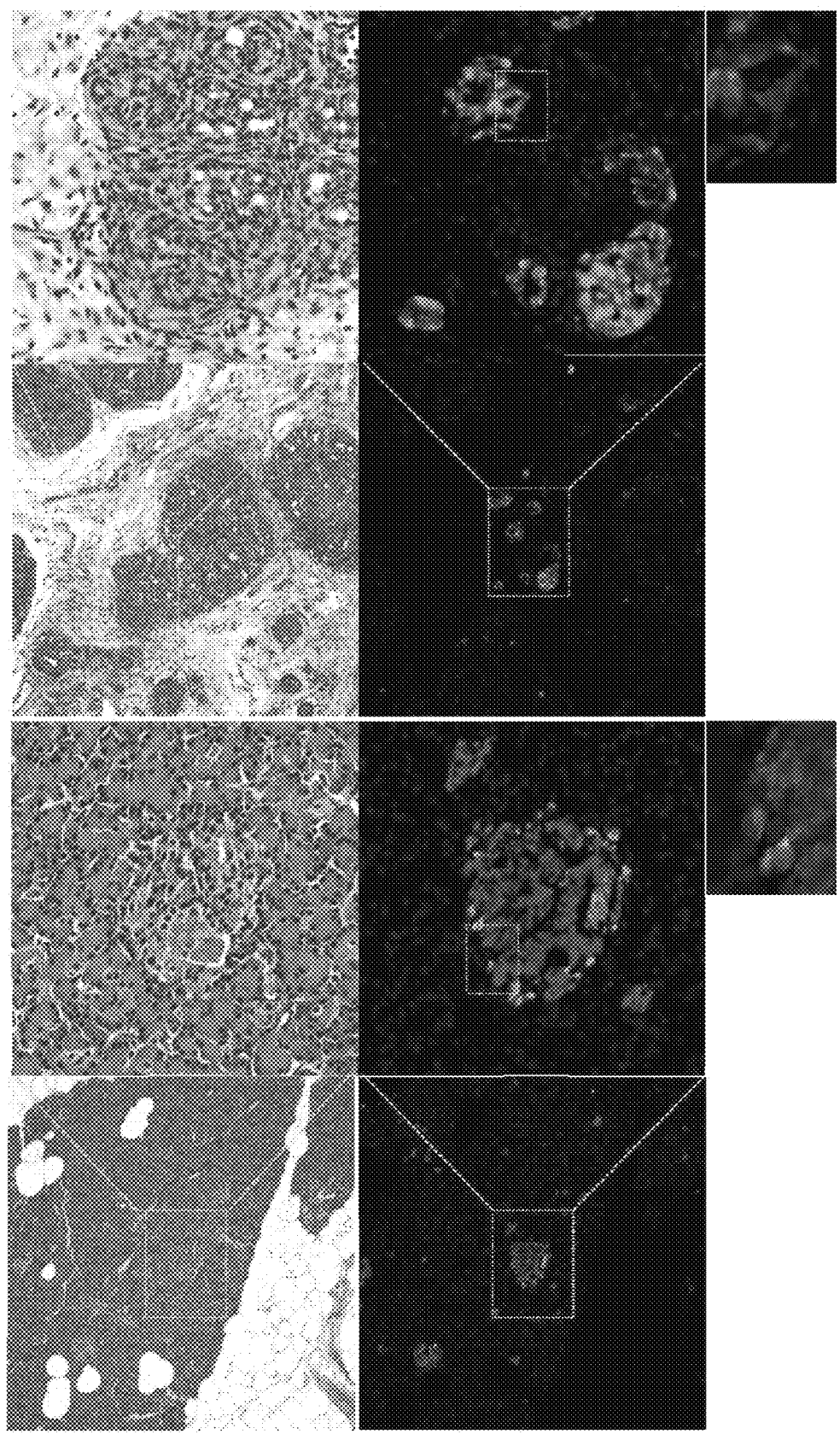
FIG. 4 shows a photograph showing the result of immunostaining of the pancreatic tissue of the pig in which pancreas formation is inhibited (right) and the wild type pig (left) (38 days old). The pancreas of the pig in which pancreas formation is inhibited has a pancreatic islet-like structure including a glucagon-producing cell but production of insulin was not observed.

2) Blood Biochemical Parameters:

Blood biochemical parameters for the pig in which pancreas formation is inhibited (FIG. 3) indicate that insulin production remained abolished and glucagon production occured as the pig grew. Glucagon production was also confirmed by immunostaining of the developed pancreatic tissue (FIG. 4). In contrast, no insulin production was observed by immunostaining of the pancreatic tissue, either (FIG. 4).

Figure 5:
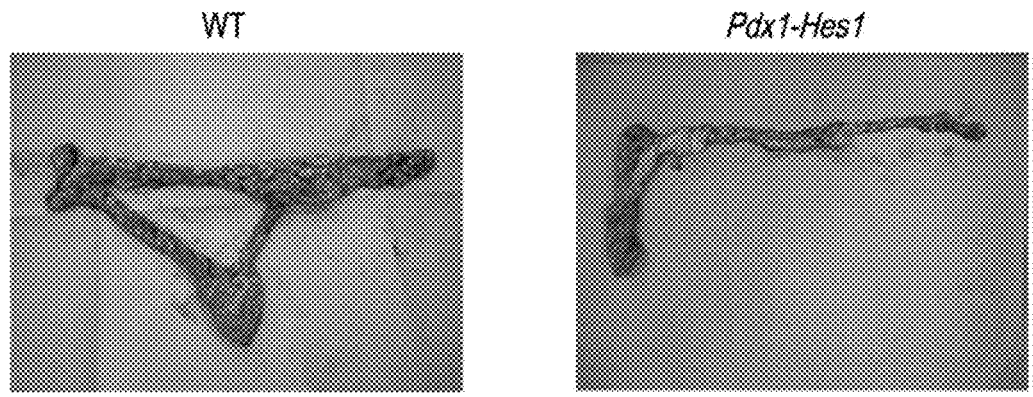
FIG. 5 shows a photograph of a secondary pancreas of the pig in which pancreas formation is inhibited (right) developed by supported raising (raising supported by administration of insulin and a digestive enzyme), and the pancreas of the wild type pig (left). It has an enough capacity for injecting cells from the outside.
Figure 6:
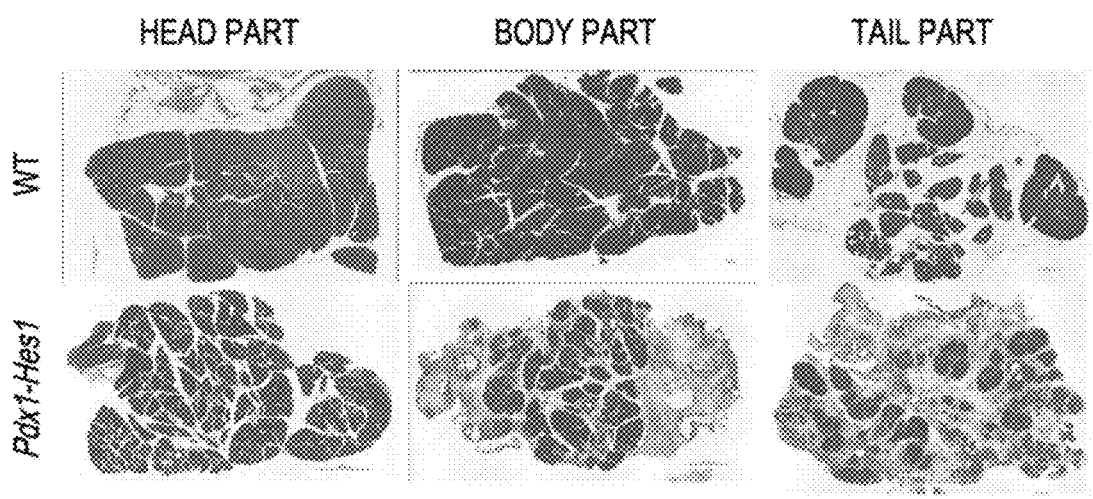
FIG. 6 shows a photograph showing HE staining of the pancreatic tissue of the pig in which pancreas formation is inhibited developed by supported raising (lower row) and the pancreatic tissue of the wild type pig (upper row). The lobule of the pig in which pancreas formation is inhibited was smaller than the lobule of the wild type pig, but included tissues other than β cells.

3) Development of Pancreas:

Supported raising of the newborn piglet in which pancreas formation is inhibited led to development of the rudimentary pancreatic tissue (FIGS. 5 and 6). Although the pancreatic tissue was about one tenth as big as a wild type pancreatic tissue (FIG. 7), amylase production was also observed (FIG. 8).

Example 4

Transplantation of Autologous Cells into Pancreatic Tissue Lacking β Cell

The pancreatic tissue developed by supported raising of the newborn piglet in which pancreas formation is inhibited lacks a β cell, which is a specific functional cell, but has other functional cells and tissue. Therefore, it is presumed that transplanting into this tissue a progenitor cell of the specific functional cell or a pluripotent stem cell whose differentiation was appropriately induced allows for establishment and growth of the specific functional cell.

Figure 9:
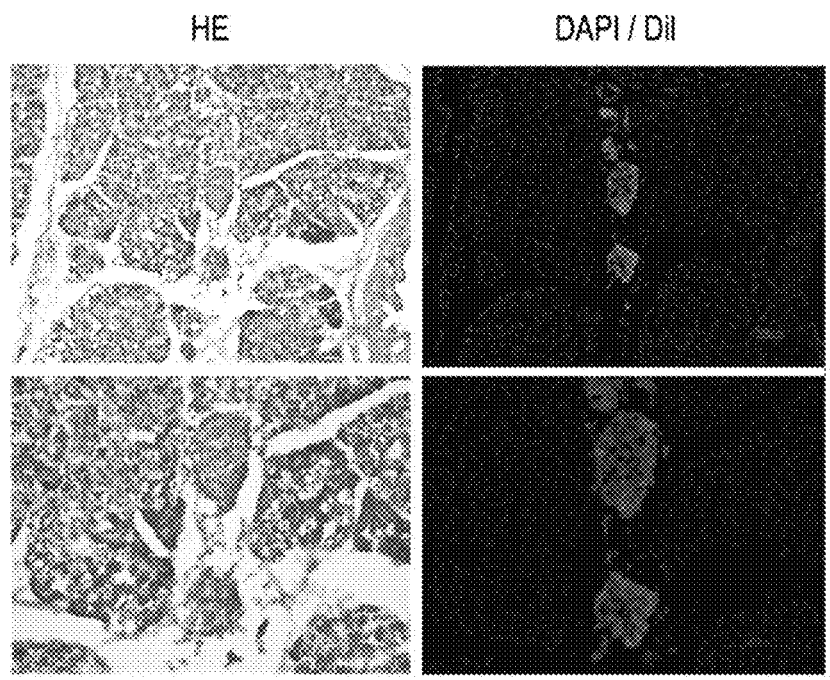
FIG. 9 shows a photograph of the pancreatic tissue of the pig in which pancreas formation is inhibited implanted with a fibroblast. The left photograph is an HE staining image and the right photograph is a fluorescent image. The transplanted fibroblast is stained with CM-DiI.

To verify this, autologous cells (fibroblasts) were injected into the pancreatic tissue of a 3.5-month-old pig in which pancreas formation is inhibited. Consequently, the autologous cells formed a colony (FIG. 9). It is presumed that when the cell to be transplanted is a progenitor cell of a β cell or a pluripotent stem cell, β cells can be formed and grown by utilizing the environment of the pancreatic tissue. Specifically, it is believed that human pancreatic functional cells (for example, β cells) can be developed by allowing human pluripotent stem cells to establish themselves in the environment within the developing pancreatic tissue of the pig in which pancreas formation is inhibited.

Example 5

Disease of Pig in which Pancreas Formation is Inhibited

1) Diabetic Retinopathy

Figure 10:
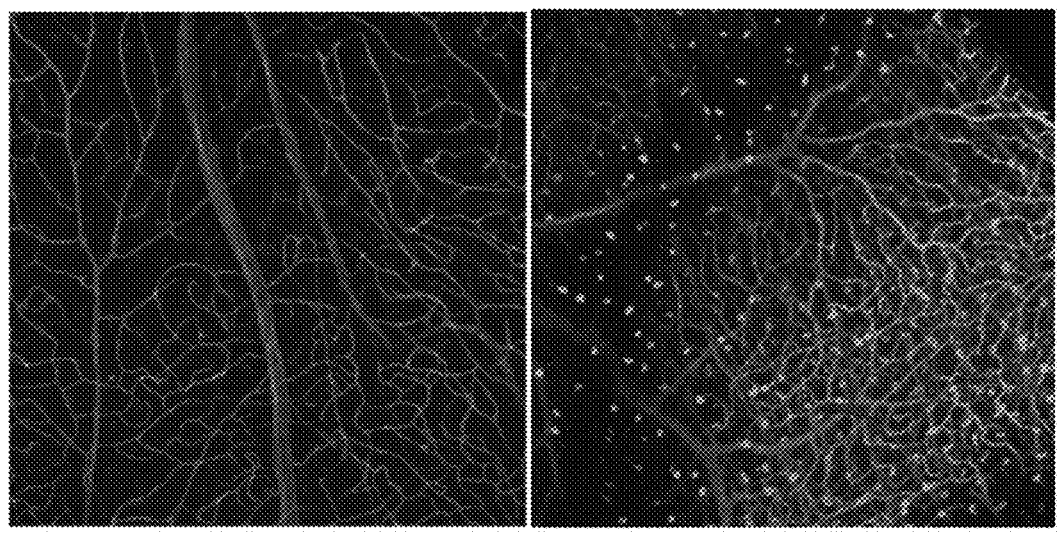
FIG. 10 shows an immunohistochemical staining image of the retina of the pig in which pancreas formation is inhibited (right) and the wild type pig (left). In the retina of the pig in which pancreas formation is inhibited, a neovessel has developed due to diabetic retinopathy.

A newborn piglet in which pancreas formation is inhibited was raised according to the method described in Example 2. The immunohistochemically stained image of the retina was observed after 80 days of raising and a pathological image characteristic of diabetic retinopathy was identified (FIG. 10). On the other hand, the retina of a wild type pig was healthy after raising for the same length of time (FIG. 10).

2) Cataract

Figure 11:
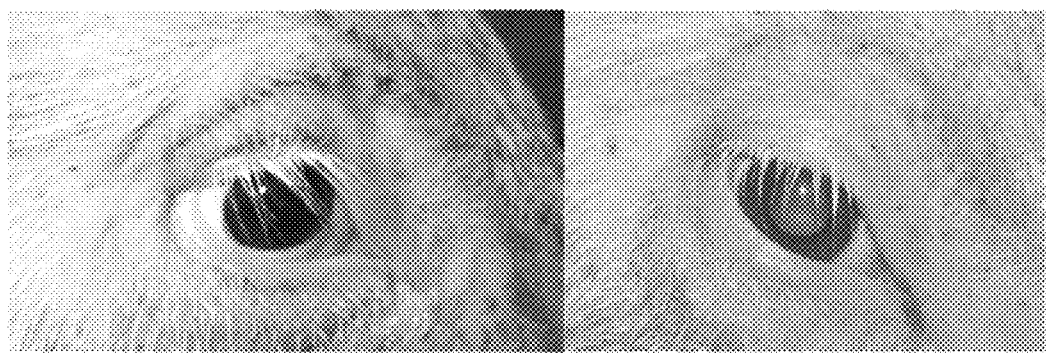
FIG. 11 shows a photograph of the right eye of the pig in which pancreas formation is inhibited (right) and the wild type pig (left). The pig in which pancreas formation is inhibited has developed a cataract characteristic of diabetes.

A newborn piglet in which pancreas formation is inhibited was raised according to the method described in Example 2. The eye was observed after 39 days of raising and development of cataract was identified (FIG. 11). On the other hand, the eye of a wild type pig was healthy after raising for the same length of time (FIG. 11).

All publications, patents, and patent applications cited herein are incorporated herein by reference in their entirety.

INDUSTRIAL APPLICABILITY

The present invention relates to a non-human animal that has a secondary organ lacking a specific functional cell, and thus, is applicable to the field of industry that handles such an animal.

The invention claimed is:

1. A method for developing a secondary organ of a pancreas in a newborn, non-human mammal, said method comprising the step of:
   administering insulin and a digestive enzyme to said newborn, non-human mammal whose genome comprises a heterologous nucleic acid encoding Hes1 operably linked to a Pdx1 promoter;
   wherein said administering of said insulin and digestive enzyme promotes formation of said secondary organ; and
   wherein said secondary organ lacks formation of β cells, and includes glucagon-expressing cells and amylase-expressing cells.

2. The method according to claim 1, wherein the secondary organ of a pancreas develops in such a manner that at least a part of the function of producing insulin and a digestive enzyme is impaired.

3. The method according to claim 1, wherein the non-human animal is a pig.

4. A non-human animal comprising a secondary organ of a pancreas lacking formation of β cells and including glucagon-expressing cells and amylase-expressing cells, wherein said animal is obtained by administering insulin and a digestive enzyme to a non-human animal newborn comprising in its genome a heterologous nucleic acid encoding Hes1 operably linked to a Pdx1 promoter, wherein development of a pancreas is inhibited by expression of said heterologous nucleic acid in said newborn and said administering results in formation of said secondary organ in said newborn.

5. The non-human animal according to claim 4, wherein the non-human animal is a pig.

6. A secondary organ of a pancreas lacking formation of β cells and including glucagon-expressing cells and amylase-expressing cells, wherein the secondary organ is obtained by administering insulin and a digestive enzyme to a non-human animal newborn comprising in its genome a heterologous nucleic acid encoding Hes1 operably linked to a Pdx1 promoter, wherein development of a pancreas is inhibited by expression of said heterologous nucleic acid in said newborn and said administering results in formation of said secondary organ in said newborn.

7. The secondary organ of a pancreas according to claim 6, wherein the non-human animal is a pig.

8. The secondary organ of a pancreas according to claim 6, wherein a transplanted cell established itself in the secondary organ of a pancreas.

* * * * *